(12) United States Patent
Fernandez Rivas et al.

(10) Patent No.: US 12,715,212 B2
(45) Date of Patent: Aug. 25, 2026

(54) JET INJECTION SYSTEM

(71) Applicant: UNIVERSITEIT TWENTE, Enschede (NL)

(72) Inventors: David Fernandez Rivas, Enschede (NL); Loreto Alejandra Oyarte Galvez, Enschede (NL)

(73) Assignee: UNIVERSITEIT TWENTE, Enschede (NL)

( * ) Notice: Subject to any disclaimer, the term of this patent is extended or adjusted under 35 U.S.C. 154(b) by 1038 days.

(21) Appl. No.: 17/436,691

(22) PCT Filed: Mar. 6, 2020

(86) PCT No.: PCT/EP2020/056037
§ 371 (c)(1), (2) Date: Sep. 7, 2021

(87) PCT Pub. No.: WO2020/182665
PCT Pub. Date: Sep. 17, 2020

(65) Prior Publication Data

US 2022/0153028 A1 May 19, 2022

(30) Foreign Application Priority Data

Mar. 8, 2019 (EP) .................................... 19161647

(51) Int. Cl.
*B41J 2/14* (2006.01)
*A61M 5/20* (2006.01)
(Continued)

(52) U.S. Cl.
CPC ............ *B41J 2/14104* (2013.01); *A61M 5/30* (2013.01); *B01L 3/5027* (2013.01); *A61M 5/204* (2013.01);
(Continued)

(58) Field of Classification Search
CPC .... A61M 5/30; A61M 5/3007; A61M 5/2046; A61M 5/2053; A61M 2005/14204;
(Continued)

(56) References Cited

U.S. PATENT DOCUMENTS 5,548,894 A 8/1996 Muto
2012/0264207 A1* 10/2012 Sharpe ................ A01N 1/0268 435/307.1
(Continued)

FOREIGN PATENT DOCUMENTS

EP 0609080 A2 8/1994
EP 2388032 A1 11/2011
(Continued)

OTHER PUBLICATIONS

Ghobad Amini, Ali Dolatabadi; Capillary instability of elliptic liquid jets. Physics of Fluids Aug. 1, 2011; 23 (8): 084109. https://doi.org/10.1063/1.3626550 (Year: 2011).*
(Continued)

*Primary Examiner* — Michael J Tsai
*Assistant Examiner* — Forrest B Dipert
(74) *Attorney, Agent, or Firm* — Pierce Atwood LLP; Christopher A. Baxter

(57) ABSTRACT

A jet injection system (10) comprising (i) a microfluidic device (100) for jet ejection and (ii) a laser-based heating system (200), wherein: —the microfluidic device (100) comprises a hosting chamber (110) defined by a chamber wall (120), the hosting chamber (110) having a chamber height hc selected from the range of 5-400 μm, a chamber width wc selected from the range of 2hc-10hc, and a chamber length $l_c$ defined by a first chamber end (111) and a second chamber end (112), wherein the second chamber end (112) comprises a first chamber opening (131) for jet ejection from the hosting chamber (110), and wherein the
(Continued)

hosting chamber (110) is configured to host a liquid (50); —the laser-based heating system (200) is configured to provide laser radiation (201) to one or more of the chamber wall (120) and a liquid (50) in the hosting chamber (110).

17 Claims, 3 Drawing Sheets

(51) Int. Cl.
*A61M 5/30* (2006.01)
*B01L 3/00* (2006.01)
*B29C 64/209* (2017.01)
*B29C 64/268* (2017.01)

(52) U.S. Cl.
CPC ..... *A61M 5/2046* (2013.01); *A61M 2205/368* (2013.01); *B01L 2300/087* (2013.01); *B01L 2300/1811* (2013.01); *B29C 64/209* (2017.08); *B29C 64/268* (2017.08)

(58) Field of Classification Search
CPC .......... A61N 1/30; A61N 1/303; A61N 1/325; A61N 1/0412; A61N 1/0428; A61N 1/0448; A61B 2017/32032; B05B 7/1686; B41J 2/14104; B41J 2/14209; B41J 2/442; B41J 2/45; B41J 2/455
See application file for complete search history.

(56) References Cited

U.S. PATENT DOCUMENTS

2016/0256106 A1* 9/2016 Krasnow ............ A61B 5/15109
2017/0282555 A1* 10/2017 De Meutter ........... B41J 2/1433
2018/0086062 A1* 3/2018 Irokawa ..................... B41J 2/16

FOREIGN PATENT DOCUMENTS

JP 2000043257 A 2/2000
JP 2005034997 A 2/2005
JP 2011067999 A 4/2011

OTHER PUBLICATIONS

International Search Report and Written Opinion dated May 26, 2020 for PCT Application No. PCT/EP2020/056037, 14 pages.
Yoshiyuki Tagawa et al: "Highly Focused Supersonic Microjets", Physical Review X, vol. 2, No. 3, Jul. 1, 2012 (Jul. 1, 2012), XP055611242, DOI: 10.1103/PhysRevX.2.031002 column 2, paragraph 3-•-figure lb, 10 pages.

* cited by examiner

JET INJECTION SYSTEM

CROSS-REFERENCE TO RELATED APPLICATIONS

This application is a National Stage 371 application claiming the benefit of International Application No. PCT/EP2020/056037, filed Mar. 6, 2020, which claims priority from European Application No. 19161647.3, filed Mar. 8, 2019, the entire contents of which are incorporated herein by reference.

FIELD OF THE INVENTION

The invention relates to a jet injection system comprising a microfluidic device for jet ejection. The invention further relates to a microfluidic device for jet ejection. The invention further relates to a method for ejecting a jet (from a microfluidic device).

BACKGROUND OF THE INVENTION

Microfluidic jet ejection devices are known in the art. For example, EP2388032A1 describes a device for creating at least one microfluidic jet, includes at least one conduit section, open to an environment of the device at one end thereof. It further includes at least one arrangement for forming in at least one of the conduit sections a meniscus forming an interface between liquid in the conduit section and the environment, at a position within the conduit section. The meniscus is at least partially concave, seen looking into the conduit section through the end open to the environment. The device includes at least one holder for holding liquid, in fluid communication with at least one of the conduit sections. It also includes at least one device for delivering an energy pulse to liquid in at least one of the holders, configured to create a shock front propagating to the meniscus and causing at least a first stage of a jet to emerge from a central part of the meniscus.

Tagawa et al., "Highly focused Supersonic Microjets", Physical Review X, vol. 2, no. 3, 1 Jul. 2012, describes the production of thin, focused jets by the rapid vaporization of a small mass of liquid in an open-ended liquid-filled capillary.

JP2011067999A describes a method of ejecting liquid and a liquid ejection device. It describes that an opening area of a nozzle at a side ejecting ink of 8 mPa second or more is ⅙ or smaller of an opening area of an ink supply channel at a pressure chamber side. It further describes that an ejection pulse PS includes a first waveform section in which electric potential is varied from reference electric potential to operational electric potential at a constant slope so as to expand the pressure chamber, a second waveform section in which the operational electric potential is maintained for a predetermined period of time and a third waveform section in which the electric potential is varied from the operational electric potential to the reference electric potential at a constant slope so as to pressurize the inside of the pressure chamber.

JP2000043257A describes a printing apparatus equipped with an ink-jet device consisting of an ink-jet head and its manufacture. Specifically, it describes an ink-jet head essentially consisting of a substrate constituting an ink pressure chamber, a diaphragm for forming a plurality of parallel grooves, and a nozzle plate having nozzle holes jointed to the side of open ends of the grooves. The diaphragm is molded so that it can be removed by a chemical process or a heat treatment. Alternatively, a composition for forming the diaphragm is molded by a printing layer method, thereby obtaining the diaphragm of a cross section having a thickness at a top part 15-60% larger than a minimum thickness of the diaphragm.

JP2005034997A describes a liquid ejection head arranged to eject a liquid drop from a nozzle opening by utilizing a pressure variation of liquid in a pressure chamber, wherein the pressure chamber cavity section consists of a flat and shallow groove section elongated in a direction intersecting the arranging direction of the pressure chambers perpendicularly and having one end communicating with a reservoir through a supply opening, and a through hole section penetrating a channel substrate and interconnecting the other end of the shallow groove section with the nozzle opening.

U.S. Pat. No. 5,548,894A describes a method of manufacturing an ink jet head including an ink-chamber member having ink chambers, and a nozzle plate secured to a front end face of the ink-chamber member and which has ink-jet holes communicating with the respective ink chambers, wherein a blank for the nozzle plate is formed by injection molding, such that blind holes are formed in one of opposite surfaces of the blank and such that each blind hole has a varying-area portion whose cross sectional area decreases in a direction from the above-indicated one of opposite surfaces of the blank toward the other surface, and the blank is subjected to laser-cutting to prepare the nozzle plate having orifice holes which cooperate with the blind holes to form the ink-jet holes.

EP0609080A2 describes an ink jet apparatus having a piezoelectric ceramic arrangement including a plurality of grooves filled with ink. The grooves are separated from one another by side walls, and the inside of the grooves are partially furnished with electrodes. The electrodes receive a driving voltage to selectively vary the inner volumes of the grooves based on the piezoelectric thickness slip effect. The selectively varied inner volumes of the grooves cause the ink to jet out therefrom. In this structure, the height of the side walls divided by the width thereof is at least 2 and at most 9.

SUMMARY OF THE INVENTION

Needle-free injection of fluids, such as insulin and inks, has a multitude of applications, including, among others, (i) cosmetic, medical and veterinary injection of medicine, pigments, etc., (ii) industrial applications where localized delivery of a liquid is required, such as for the functionalization of a coating, and (iii) 3D-printing applications. For example, needle-free fluid injection can be used in health-related applications such as devices for needle-free injection that can be deployed as Point-of-Care devices for painless medicine/vaccination delivery, or in cosmetic restoration of skin pigmentation for burnt patients, vitiligo, permanent make-up or tattooing.

The principle of needle-free fluid injection may be the ejection of a jet capable of penetrating a target material, such as a human skin, from a jet ejection system.

With respect to needle-based injection systems, jet injection systems may be preferable for various reasons, including, among others, needle phobia, needle-related pain, waste of needles, needle contamination, and accidental needle contact, wherein the latter two may further contribute to the inadvertent spread of diseases.

Jet ejection systems known in the prior art may, however, suffer from one or more drawbacks, including: low jet velocity (no penetration), too high jet velocity (tissue damage/too deep penetration), jet splashback, low jet volume, too high jet volume (liquid pours out again/may cause splashback), low jet stability, too large jet diameter, low jet injection depth, expensive system components, noise-generation, energy-inefficiency, substantial energy demands, low jet ejection frequency, and fragility of the ejection capillary/chamber. Further, prior art jet injection systems may be inconsistent in one or more of jet velocity, jet volume, jet stability and jet diameter. Further, prior art jet injection systems may provide no or poor control over one or more of jet velocity, jet volume, jet stability and jet diameter.

For example, a prior art jet ejection system may involve rapid vaporization of a liquid in an open liquid-filled capillary via an energy pulse. This rapid vaporization may involve substantial energy demands, resulting in the jet ejection system being both energy-inefficient and unsuitable for mobile devices, such as unsuitable for handheld devices for private and/or on-site use. Handheld jet injection devices may be desired for, for example, insulin or painkiller injections at home, or for veterinary applications at a farm. It is expected that patient compliance will improve with needle-free injections. Additionally, for permanent make up applications, where nowadays microblading or conventional tattoo machines are used, a jet injector may provide higher resolution (spot size) and virtually no damage to the skin injected into.

Another prior art jet ejection system may, for example, provide droplet generation from the transformation of a single bubble in a nanofluidic channel by a laser-induced jet. However, the prior art jet ejection system may provide jets with a volume in the femtoliter-scale, which may be too small for (many) practical applications.

Yet another prior art jet ejection system may, for example, generate a jet via one of pressurized air, springs, or coil actuators, all of which apply high-mechanical pressure and may be noisy, painful, variable in provided energy resulting in different liquid jet properties, cumbersome to use, too large for portable use, etc.

Hence, it is an aspect of the invention to provide an alternative jet injection system, which preferably further at least partly obviates one or more of above-described drawbacks. The present invention may have as object to overcome or ameliorate at least one of the disadvantages of the prior art, or to provide a useful alternative.

Therefore, in a first aspect, the invention provides a jet injection system ("system") comprising (i) a microfluidic device for jet ejection ("liquid jet ejection") and (ii) a laser-based heating system. The microfluidic device comprises a hosting chamber (essentially) defined by a chamber wall. The hosting chamber may especially be configured to host a liquid. In specific embodiments, the hosting chamber has especially a chamber height $h_c$ selected from the range of 5-400 μm, especially a chamber width $w_c$ selected from the range of $2h_c$-$10h_c$, and especially a chamber length $l_c$ defined by a first chamber end and a second chamber end. The second chamber end comprises a first chamber opening for jet ejection from the hosting chamber, especially for jet ejection from the hosting chamber of at least part of the liquid. The laser-based heating system is configured to provide laser radiation to one or more of the chamber wall and a liquid in the hosting chamber. Especially, the laser-based heating system is configured to provide the laser radiation to the chamber wall and/or to the liquid in the chamber (at a location) closer to the first chamber end than to the second chamber end. Due to the laser radiation, a liquid jet is generated and escapes via the first chamber opening (in the second chamber end).

The system according to the invention provides the benefit that jets may be consistently ejected with an appropriate force, stability, and diameter to result in the penetration of a target material, such as a human skin, with a relatively low energy requirement. During operation of the system, laser radiation may be applied to the chamber wall and/or the liquid such that the liquid is brought to a boil, resulting in the creation of a fast-expanding bubble which may, for example, have velocities in the range of 10-100 m/s. The expansion of the bubble is a conversion of at least part of the laser radiation energy into kinetic energy that is transferred to the liquid that is set in motion. Especially, the microfluidic device may be configured such that the fast-expanding bubble moves towards the second chamber end and thereby transfers kinetic energy to the liquid, which results in the formation of a jet ejected from the second chamber end. Especially, the bubble has a bubble edge (also "bubble surface" or "bubble wall") moving towards the second chamber end and thereby transfers kinetic energy to the liquid, which results in the formation of a jet ejected from the second chamber end. The term "bubble edge" may herein refer to the surface (area) of the bubble closest to the second chamber end. Specifically, the term "bubble edge" may herein refer to the interface between the bubble and the liquid.

As the liquid may be brought to a boil, the required energy input may be substantially lower than in prior art systems involving instant vaporization. Further, the system according to the invention may provide more control on the jet volume, jet velocity, jet diameter and jet length relative to prior art systems. Further the system according to the invention may have reduced splash back relative to prior art systems. Yet further, the system according to the invention may be portable, non-noisy and capable of delivering doses in a fast and energy efficient manner. Further, the chamber can be reused for more than several hundred injections with a substantially reduced, especially without, risk of breakage relative to prior art, e.g. capillaries.

The indicated chamber geometries, particularly the height $h_c$ and width $w_c$, may provide beneficial jet ejection properties. If these dimensions are too small, the jet properties may be negatively affected through (relatively large) interactions between the chamber wall and the (to-be ejected) liquid ("wall effect"), especially due to shear stress. If these dimensions are too large, the jet properties may be negatively affected due to one or more of inconsistent bubble movement (too many available directions) and the (too large) volume of the liquid to displace.

In general, the term "jet" may refer to a natural or man-made collimated stream of matter. For example, generating a jet (also: "jetting") may be possible from small orifices or nozzles. Herein, the term "jet" refers to a high-velocity and low-diameter stream of liquid forced out of a (small) opening, especially forced out of the second chamber end. A jet may have a velocity of at least 1 m/s. The jet may have high stability i.e., the jet may essentially comprise a substantially continuous, especially unbroken, liquid stream, in contrast to a stream of successive individual droplets. The jet may have a diameter selected from the range of 10-500 μm, especially selected from the range of 25-300 μm, such as selected from the range of 50-150 μm. It will be clear to the person skilled in the art that jet injection in different types of subjects may require different jet properties, such as different jet velocities and/or diameters. For example, for jet injection in a human skin a jet may need to have a velocity of at least about 14 m/s.

As will be clear to the person skilled in the art, for injection into a human skin, an ejected liquid may need to have a sufficient ballistic energy to penetrate the outer layer of the skin. The ballistic energy may be related not only to the velocity, but also to mass and density. Hence, for example, a spherical droplet and an elongated jet with a sharp tip may have substantially different penetration potential, even when they comprise the same liquid and travel at the same velocity.

A jet injection system (also: "jet ejection system" or "system") is a system configured for the generation (and ejection) of j ets, and especially also for the injection of jets in a subject. The jet injection system may, in embodiments, be configured to be arranged on a subject to inject a jet into the subject. In further embodiments, the jet injection system may comprise a distance holder for arranging the jet injection system on a subject with a predetermined distance between the second chamber end and the subject. In further embodiments, the jet injection system may be configured to eject jets onto or against a subject, i.e., the jet injection system may also be applied for jet ejection applications other than jet injection. For example, to bounce against the skin and splash back against a third object, such as especially the sensor of a wearable device. Prior art wearable devices may suffer from poor positioning against the skin, and unreliable sampling of, for example, sweat. With a controlled jet splashing back against skin, and landing on a sensor surface, you may have a reproducible way to measure the concentration of ions or other molecules in the sweat or present at the skin surface. The jet injection system may also be used for injecting liquid in the eye, e.g. injections are often used to treat several conditions on the eye, specifically the macular body. Avastin (anti-VEGF) may be used for treating exudative macular degeneration, as an endothelial growth factor. The standard treatment may require around 10 to 14 injections, two to three times per week, distributed in a period of a month. In each injection, approximately 0.05 mL may be administered with a 30G needle (yellow), similar to the one used for insulin injections. This procedure of intravitreal injection may have a 0.03% risk of infection (endophthalmitis). Similarly for anesthesia injection in the gum during dental procedures.

Microfluidic devices (also "microfluidic platforms" or "microfluidic systems") comprise a broad range of devices related to the field of microfluidics. The field of microfluidics may deal with the behavior, control and manipulation of fluids, typically in small volumes, such as volumes on the order of μl, nl, pl, and fl. Microfluidic devices may be able to precisely control and manipulate fluids on a micrometer-size down to a sub-micrometer-size scale. The channels or features present on a chip may be obtained through a process comprising lithography, dry etching, wet etching, soft-lithography and/or bonding, but may also be provided with other (new) techniques such as laser ablation. The microfluidic device of the present invention may especially be configured for (liquid) jet ejection.

The terms chamber and channel refer herein to a space in a microfluidic device. The term "channel" may especially refer to an elongated space, such as a tube, duct, pipe, or conduit, suitable for the transportation of a fluid. A channel may especially be elongated along one dimension with respect to the other dimensions. The term "chamber" may especially refer to a space wherein two dimensions are lengthened with respect to a third dimension, especially with respect to a height. As is clear to a person skilled in the art, chambers and channels in microfluidics devices may in general be in fluid connection to a chamber-specific or channel-specific reservoir for providing and/or removing of a fluid, especially a liquid.

The hosting chamber (also: "chamber") is configured to host a liquid, especially a to-be ejected liquid. The hosting chamber is defined by a chamber wall, especially by an inner chamber surface of the chamber wall. The hosting chamber has a first chamber end and a second chamber end along a chamber axis A (also "axis of elongation") parallel to the chamber length. The hosting chamber may substantially be closed except for a first opening at the second chamber end for jet ejection, and a second opening configured for providing a liquid to the hosting chamber (and/or for removing a liquid from the hosting chamber). The second opening may especially be functionally coupled to a fluid supply channel.

The hosting chamber may in embodiments have three chamber dimensions: a chamber height $h_c$, a chamber width $w_c$ and a chamber length $l_c$. The chamber height $h_c$ may be selected from the range of 5-400 μm, such as from the range of 10-300 μm, especially from the range of 20-250 μm, such as from the range of 40-200 μm, especially 50-150 μm, such as from the range of 80-120 μm. The chamber width $w_c$ may be selected from the range of $1h_c$-$12h_c$, such as from the range of $2h_c$-$10h_c$, especially from the range of $3h_c$-$6h_c$. In specific embodiments, the chamber width $w_c$ may be selected from the range of $3h_c$-$4.5h_c$, or the chamber width $w_c$ may be selected from the range of $5.5h_c$-$6h_c$, or especially from the range of $5.5h_c$-$6.5h_c$, such as from the range of $5.75h_c$-$6.25h_c$.

In further embodiments, the chamber width $w_c$ may be at least 100 μm.

In a specific embodiment, the chamber height $h_c$ may be about 100 μm. In a further embodiment, the chamber width $w_c$ may be selected from the range of 575-625 μm.

In embodiments, the chamber wall may comprise five wall segments: the first chamber end, a top wall segment and a bottom wall segment in planes perpendicular to the chamber height $h_c$, and two side wall segments in planes perpendicular to the chamber width $w_c$. In general, an edge between two wall segments may be rounded. For example, the edge between the top wall segment and any one of the two side wall segments may be rounded. Similarly, the corner between two wall segments and the first chamber end may be rounded. Rounded edges may reduce the interactions between the chamber wall and the (to-be ejected) liquid ("wall effect") relative to 90° angles between two adjacent wall segments. Hence, in embodiments, the chamber wall defines rounded edges (for the hosting chamber), especially the rounded edges may essentially be shaped as a partial circle, such as a quarter of a circle.

Especially, the first chamber end is a wall segment opposite of the open-ended second chamber end. The second chamber end may comprise the first chamber opening configured for allowing jet ejection from the chamber. Especially, the second chamber end (essentially) is the first chamber opening configured for allowing jet ejection from the chamber.

The laser-based heating system is configured to provide laser radiation to one or more of the chamber wall and a liquid in the hosting chamber. Hence, the laser-based system may especially be configured to irradiate one or more of the chamber wall and a liquid in the hosting chamber. The jet injection system, especially the laser-based heating system, is configured to bring the liquid in the hosting chamber to a boil by providing laser radiation. In embodiments, the laser-based heating system comprises a non-pulsed and/or low-energy laser system, especially, the laser-based heating system may comprise a laser system selected from the group comprising a continuous wave laser system, a laser diode system, and an LED-based laser system, especially from the group comprising a continuous wave laser system, and an LED-based laser system, more especially the laser-based heating system may comprise a continuous wave laser system.

A continuous wave laser system may be beneficial with regards to a pulse-based laser system in that it may be cheaper, more energy-efficient, and may require less cooling. In particular, a continuous wave laser system may be passively cooled, such as without the use of fans, liquids, and (aluminum) heat dissipaters.

For instance, the laser-based heating system may provide focused laser light with a focal point at a part of the chamber wall or close to the chamber wall (but within the hosting chamber), thereby effectively heating the liquid in the chamber. When the chamber wall is irradiated with laser light, it will in general be at a position at the chamber wall where the chamber wall is in physical contact with the liquid. Hence, in general the laser light will at least partly penetrate into the liquid (even when the wall of the hosting chamber is irradiated). The term "irradiating the wall" and similar terms may especially refer to (at least) irradiation of an inner chamber surface of the chamber wall that defines the hosting chamber; see further also below.

In general, the laser-based heating system may be configured to provide the laser radiation to the chamber wall and/or to the liquid in the chamber (at a location) closer to the first chamber end than to the second chamber end. The location at which the radiation is provided may affect the consistency and/or volume of the jet ejection. If the laser radiation is provided at the first chamber end resulting in the formation of a bubble at the first chamber end, the bubble (i) can only move/expand towards the second chamber end, and the majority of the liquid in the hosting chamber will be displaced as it is between the bubble formation location and the second chamber end. In contrast, if the bubble is formed halfway between the first chamber end and the second chamber end, the bubble may move/expand either towards the first chamber end or the second chamber end, and less of the liquid is between the bubble formation location and the second chamber end.

It will be clear to the person skilled in the art that an application may require a minimum injection volume. For example, for medical tattooing, a volume of about 10 pL of ink may be required to provide a "dot". It will further be clear to the person skilled in the art that the required injection volume may depend on how deep the injections is, as deeper injections may, for example, fade ink. Hence, in embodiments, the jet injection system may be configured to provide a jet volume of at least 10 pl, such as a jet volume of at least 20 pl, especially at least 50 pl, such as at least 100 pl, especially at least 500 pl, such as at least 1 nl, especially at least 10 nl, such as at least 20 nl, especially at least 50 nl, such as at least 100 nl. In specific embodiments, the jet volume may be up to about 250 nl, such as selected from the range of 10-200 nl.

For example, in experiments, an embodiment of the jet injection system was employed to eject jets with jet volumes of up to 150 nl with a repetition frequency of about 200 Hz.

In embodiments, the laser-based heating system may be configured to provide the laser radiation via one or more optical elements, such as one or more optical elements selected from the group comprising optical fibers, mirrors, and lenses, especially via one or more optical fibers.

The laser radiation may be provided to the chamber wall and/or to the liquid. Hence, in embodiments the chamber wall may be heated by the laser radiation, thereby indirectly heating the liquid. In further embodiments, the liquid may be heated directly by the laser radiation.

Hence, in embodiments, at least part of the chamber wall may be light transmissive for the laser radiation. In such embodiments, the laser radiation may be provided directly to the liquid.

In further embodiments, at least part of the chamber wall may comprise a material configured to absorb the laser radiation. In such embodiments, the laser radiation may be provided to heat the chamber wall, thereby indirectly heating the liquid. In further embodiments, at least part of the chamber wall may comprise a (compounded) absorption material configured to absorb the laser radiation, especially at least part of the chamber wall may comprise a plating of absorption material configured to absorb the laser radiation. Hence, the absorption material may be selected to be suitable to absorb one or more wavelengths comprised by the laser radiation.

In yet further embodiments, the absorption material may comprise a material suitable to absorb one or more wavelengths comprised by the laser radiation. Especially, the (compounded) absorption material may comprise one or more metals selected from the group consisting of gold, copper, silver, aluminum, especially gold. Hence, in specific embodiments, at least part of the chamber wall may comprise gold configured to absorb the laser radiation, especially at least part of the chamber wall may comprise a gold plating configured to absorb the laser radiation.

In yet further embodiments, the absorption material, especially the gold, such as the gold plating, may be configured such that exposure of the absorption material to the laser radiation results in surface plasmon generation. Especially, the absorption material may comprise 2D (metal) nanostructures arranged to provide surface plasmon resonance when irradiated with the laser radiation.

In further embodiments, the jet injection system, especially the laser-based heating system, may be configured to provide the laser radiation to the chamber wall and to the liquid in the chamber. Hence, at least part of the chamber wall may be light transmissive for the laser radiation and/or at least part of the chamber wall may comprise a material configured to absorb the laser radiation.

During operation, the bubble, especially the bubble edge, formed by the boiling of the liquid in the hosting chamber may move towards the second chamber end, thereby displacing the liquid in the hosting chamber and forming a jet at the second chamber end. The liquid displacement may depend on interactions between the liquid and the chamber wall. Hence, in embodiments, the chamber wall may comprise an inner chamber surface, wherein at least part of the inner chamber surface is hydrophobic, especially wherein a hydrophobic coating is arranged on at least part of the inner chamber surface. In further embodiments, the chamber wall may comprise an inner chamber surface, wherein at least part of the inner chamber surface is hydrophilic, especially wherein a hydrophilic coating is arranged on at least part of the inner chamber surface. The hydrophobic and/or hydrophilic inner chamber surfaces may be configured to provide attraction and/or repulsion between the liquid and the inner wall surface near the second chamber end, e.g., if the liquid is an aqueous solution, the inner wall surface near the second chamber end may be hydrophobic to reduce attraction/ increase repulsion between the liquid and the inner wall surface (near the second chamber end).

In specific embodiments, the second chamber end may be hydrophobic, especially the face of the chamber at the second chamber end may be hydrophobic, more especially wherein a hydrophobic coating is arranged on the face of the hosting chamber at the second chamber end. A hydrophobic coating on the face of the hosting chamber at the second chamber end may be beneficial as it may avert droplet formation at the second chamber end, which could otherwise interfere with a jet ejection.

In embodiments, each of the chamber dimensions may be essentially constant along the other chamber dimensions. Hence, in specific embodiments, along at least 80% of the chamber length $l_c$ the chamber height $h_c$ and chamber width $w_c$ are constant, or (when slightly not constant) one or both of the chamber height $h_c$ and chamber width $w_c$ vary with less than 10% relative to (their) respective maximum values (of the chamber height $h_c$ and chamber width $w_c$).

In further embodiments, along at least 80% of the chamber length $l_c$ the hosting chamber has a cross-sectional shape (perpendicular to chamber axis A) approximating a shape selected from the group comprising a rectangle, a rounded rectangle, a stadium, and an oval, especially, selected from the group comprising a rounded rectangle, a stadium, and an oval, such as especially an ellipse.

In further embodiments, the hosting chamber may be (essentially) symmetrical with respect to the chamber axis A. The symmetry of the hosting chamber may contribute to more consistency in jet generation and/or higher velocity of the generated jets.

In yet further embodiments, the hosting chamber may have a shape approximating a rectangular cuboid, especially a rectangular cuboid with rounded edges. Hence, the chamber wall, especially the inner chamber surface, may define a shape approximating a rectangular cuboid, especially a rectangular cuboid with rounded edges (on the inside of the chamber wall).

In embodiments, the hosting chamber may comprise a second chamber opening arranged closer to the first chamber end than to the second chamber end, especially arranged from the first chamber end at a third distance d3, wherein d3<d2. The second chamber opening may be configured for providing the liquid to the hosting chamber. The second opening may further be configured for removing the liquid to the hosting chamber.

The term "second chamber opening" may also refer to a plurality of second chamber openings, especially wherein each of the plurality of second chamber openings is configured for providing and/or removing a different liquid to the hosting chamber. In specific embodiments, one or more of the second chamber openings may be configured for providing and/or removing a gas to the hosting chamber.

In further embodiments, the jet injection system further comprises a fluid supply configured for providing a fluid, especially a liquid, to the hosting chamber. In yet further embodiments, the fluid supply is functionally coupled to the second chamber opening. The term "fluid supply" may also refer to a plurality of fluid supplies, especially liquid supplies, especially wherein each of the plurality of fluid supplies, especially liquid supplies, is configured for providing and/or removing a different fluid, especially a (different) liquid, to the hosting chamber.

Hence, in specific embodiments, the hosting chamber may comprise two or more second chamber openings functionally coupled to two or more respective liquid supplies, wherein the two or more liquid supplies are configured for providing at least two different fluids to the hosting chamber. A jet injection system configured such that two or more different fluids can be provided to the hosting chamber may provide the benefit that two or more fluids may be mixed in the hosting chamber. For example, the composition of the liquid may be changed for successive jet injections. Similarly, two or more fluids may be provided such that the concentration of one or more compounds in the (to-be ejected) liquid is as desired.

For example, in specific embodiments, the jet injection system may be functionally coupled to a sensor system configured to measure a parameter related to the subject, wherein the sensor system provides a sensor signal to the jet injection system, and wherein the jet injection system may be configured to provide two or more fluids into the hosting chamber based on the sensor signal. For example, the jet injection system may be functionally coupled to a camera configured to measure a cosmetic-related parameter from the skin of a subject, and the jet injection system may be configured to mix two or more fluids in the hosting chamber to provide a (to-be ejected) liquid with desired properties based on the sensor signal.

During operation, and prior to the providing of laser radiation, the hosting chamber may be partially filled with the liquid. In general, the hosting chamber may be filled with the liquid from the first chamber end to a second distance d2 from the first chamber end. The second distance d2≤the chamber length $l_c$, especially <$l_c$, such as ≤0.90 $l_c$, especially ≤0.8 $l_c$, such as ≤0.6 $l_c$. Hence, the jet injection system, especially the liquid supply, may be configured to provide the liquid to the hosting chamber up to the second distance d2.

In embodiments, the second distance d2 may be controlled by the amount of liquid provided to the hosting chamber.

At the second distance d2 (from the first chamber end), the liquid forms a meniscus at an interface with air. If d2 is equal to $l_c$, the meniscus forms at the second chamber end and may be substantially flat. However, in general, d2<$l_c$ and may be concave as seen from the second chamber end. In embodiments wherein the chamber width $w_c$ >the chamber height $h_c$, such as $w_c$=2$h_c$, the meniscus may comprise a double meniscus. The meniscus may facilitate higher jet velocities due to increased focusing, i.e., a more curved meniscus shape (smaller radius of curvature and lower (initial) contact angle) may provide a higher jet velocity due to increased focusing. Hence, in embodiments, the hosting chamber may be configured to provide a (double) meniscus having a curved meniscus shape.

In embodiments, the hosting chamber may be configured to provide a contact angle, especially an initial contact angle, between the meniscus and the chamber wall selected from the range of 10°-90°, especially from the range of 20°-70°, such as from the range of 25°-50°.

The liquid (or especially the meniscus) is arranged at an (initial) contact angle q with respect to the chamber wall (as seen from the first chamber end). The (initial) contact angle may depend on the material properties of the chamber, as well as on any coating or functionalization (e.g. plasma) that could be made to the chamber wall. In embodiments, the jet injection system, especially the fluid supply, may be configured to control the second distance, i.e., the second distance d2 may be controlled to provide different jet ejection properties, such as a different jet volume and/or a different jet velocity. In general, a lower d2 may result in a lower jet volume and in a higher jet velocity. However, also depending on chamber geometries, a too low value for d2 may result in unstable jet generation or even insufficient liquid for jet ejection. Hence, in embodiments, d2 may be selected such that d2≥100 μm, such as ≥150 μm, especially ≥200 μm, such as ≥250 μm, especially ≥300 μm. A 5 too low value of d2 may result in no bubble formation, for example, the liquid may be vaporized rather than heated to bubble formation if d2 is too small. It appears that especially a value of d2≥200 μm provides sufficient liquid for bubble formation.

In further embodiments, the jet injection system may be configured to have a constant second distance d2.

Hence, the jet injection system, especially the fluid supply, may be configured to control the volume of the liquid in the hosting chamber. Especially, the jet injection system may be configured to sense the volume of the liquid in the hosting chamber and adjust the volume of the liquid to a target volume. Hence, in embodiments, the jet injection system may comprise a sensor suitable for determining the volume of the liquid in the hosting chamber, such as especially a visual sensor and/or a pressure sensor and/or thermal-electric sensor.

In specific embodiments, the hosting chamber may comprise a contact line barrier arranged at a second distance d2 from the first chamber end. The contact line barrier may be configured to facilitate providing the liquid to the hosting chamber up to the second distance d2, i.e., the contact line barrier may facilitate providing the meniscus at the second distance d2 (from the first chamber end). The contact line barrier may (also) be configured to provide the meniscus at a desired angle. The meniscus may contribute to self-focusing of the jet, hence by arranging the contact line barrier such that the meniscus is provided at an angle, the jet may be focused at a desired angle. A more curved meniscus may have a more intense focusing effect (resulting in higher jet velocity) compared to flat menisci.

Hence, in further embodiments, the hosting chamber may be configured to host the liquid between the first chamber end and the contact line barrier.

In further embodiments, the contact line barrier may be selected from the group comprising an indentation and a protrusion. Hence, in embodiments, the contact line barrier may comprise a plurality of indentations and/or protrusions arranged along the chamber wall, especially arranged along the chamber wall at a distance d2 from the first chamber end. In further embodiments, the contact line barrier may comprise a single continuous indentation or protrusion arranged along the chamber wall, especially arranged along the chamber wall at a distance d2 from the first chamber end. In general, the contact line barrier may be configured perpendicular to the chamber axis A. However, in specific embodiments, the contact line barrier may be configured at an angle unequal to 90° relative to the chamber axis A, especially wherein the contact line barrier is configured to provide the meniscus at a desired angle. For example, the contact line barrier may be closer to the first chamber end at the top wall segment than at the bottom wall segment.

The jet injection system may in principle be applied for any liquid. However, in embodiments, the jet injection system may be configured for a specific liquid based on, for example, the viscosity of the liquid and/or on whether the liquid is polar or nonpolar. The liquid may comprise a single compound, but may also comprise two or more compounds; the liquid may be a solution.

In embodiments, the liquid may comprise a polar solvent. The polar solvent may comprise a solvent selected from the group comprising water, glycerol, propylene glycol and any other liquid (typically) used for injections and medical procedures, especially a solvent selected from the group comprising water, glycerol, and propylene glycol, more especially a solvent selected from the group comprising water and glycerol. Hence, in further embodiments, the jet injection system may be configured for the ejection of a (liquid comprising a) polar solvent. Especially, the hosting chamber may be configured to host a polar solvent. The liquid may comprise small molecules and/or particles of varied size. The function of molecules and particles can be varied. Particles may tend to provide more permanent effects, while molecules and smaller particles may diffuse faster and can be more easily removed by the defense mechanisms of a (human) body.

In further embodiments, the liquid may comprise a non-polar solvent, especially an organic nonpolar solvent. Hence, in further embodiments, the jet injection system may be configured for the ejection of a (organic) nonpolar solvent. Especially, the hosting chamber may be configured to host a (organic) nonpolar solvent.

In further embodiments, the liquid may comprise one or more additives. Especially, the liquid may comprise one or more additives to facilitate jet ejection. For example, in embodiments wherein the laser-based heating system is configured to provide radiation to the liquid for heating, the liquid may comprise an absorption additive suitable to absorb (one or more wavelengths of) the laser radiation. In some cases, the molecules of interest for the injection may comprise a molecule suitable to absorb the laser radiation. However, in other cases an additive may need to be added for the direct purpose of absorbing the laser radiation.

In further embodiments, the liquid may comprise an additive for increasing or reducing the viscosity of the liquid. For example, the liquid may comprise glycerin to increase the liquid viscosity.

In further embodiments, the liquid may comprise an additive to reduce and/or suppress jet break-up. In particular, the liquid may comprise an additive to modify surface tension, which may result in the reduction and/or suppression of the jet break-up. For example, the liquid may comprise polyethylene glycol (PEO) to reduce and/or suppress jet break-up, especially PEO with a molecular weight selected from the range of 10000-400000, such as PEO with a molecular weight of 10000, 90000 or 400000.

For example, the liquid may comprise an additive selected from the group comprising insulin, painkillers, vaccines, and biosensor molecules. In further embodiments, the additive may be selected from the group comprising surfactants, solvents, binders, fillers, aromatic amines, especially primary aromatic amines (PAA), and polycyclic aromatic hydrocarbons (PAH). Hence, the liquid may comprise one or more functional components (active ingredients). For instance, the liquid may comprise a (dissolved) pharmaceutical and/or a (dissolved) nutraceutical, such as for use in the treatment of a disease. Herein, the term "pharmaceutical" may refer to one or more of a drug, a diagnostic marker (such as for MM), etc.. The term "nutraceutical" may amongst others refer to a nutrient, a dietary supplement, a herbal product, etc.. The term nutraceutical may especially refer to a food product also having a pharmaceutical function.

The laser-based heating system is configured to provide the laser radiation to the chamber wall and/or to the liquid in the hosting chamber, especially such that (part of) the liquid is brought to a boil. Hence, in embodiments, the laser-based heating system may be configured to provide radiation for a heating time period of, for example, 0.1 ms-10 s, such as for a heating time period of 0.1 ms-500 ms, especially of 0.1 ms-200 ms, such as 0.2 ms-100 ms, especially 0.5-70 ms. Good results were already obtained with heating time periods between 0.1 ms-200 ms. In contrast, prior art systems configured for instant vaporization may provide radiation for a time period of about 5-500 ns, which may typically be used for pulsed lasers. A benefit of the longer time period employed in embodiments of the invention may be that the energy transfer may be more efficient, thus having a reduced energy requirement.

In embodiments, the laser-based heating system may comprise a laser system selected from the group comprising a continuous wave laser system, an LED-based laser system, and a non-pulsed low-energy laser system, especially a continuous wave laser system.

In embodiments, the laser-based heating system may be configured to provide laser radiation comprising a wavelength suitable for absorption by the chamber wall and/or the liquid, i.e., the laser radiation, especially the wavelength, may be selected such that the chamber wall, especially the absorption material, and/or the liquid, especially the absorption additive, can absorb the laser radiation. In specific embodiments, the laser-based heating system may be configured to provide laser radiation comprising a wavelength selected from the range of 200-1100 nm, such as from the range of 300-1050 nm, especially from the range of 450-975 nm.

The laser-based heating system may be configured to provide the radiation to the chamber wall and/or the liquid at a specific location and/or angle.

In general, the laser-based heating system may be configured to provide the radiation to the chamber wall and/or to the liquid closer to the first chamber end than to the second chamber end, especially to beneficially restrict (or: direct) movement of a formed bubble. Hence, in embodiments, the laser-based heating system may be configured to provide the radiation to the chamber wall and/or to the liquid within a first distance d1 from the first chamber end, wherein d1≤0.5 chamber length $l_c$, such as ≤0.41, especially ≤0.31, such as ≤0.2 $l_c$, especially ≤0.15 $l_c$, such as ≤0.1 $l_c$.

In embodiments, the laser-based heating system may be arranged at an angle from the chamber axis A selected from the range of 0°-90°.

In further embodiments, the laser-based heating system may be configured to provide the laser radiation to the hosting chamber via the (chamber wall at the) first chamber end, i.e., the laser-based heating system may be configured to provide the radiation essentially parallel to the chamber axis A. Hence, the laser-based heating system may be arranged at an angle from the chamber axis A of ≤5°, such as ≤1° including 0°. Especially, the laser-based heating system may be configured downstream from the first chamber end (as seen from the hosting chamber).

In specific embodiments, the hosting chamber may have a chamber axis A (parallel to the chamber length $l_c$), wherein the laser-based heating system is configured to provide the laser radiation to the chamber wall and/or through the chamber wall within a range defined by a first plane perpendicular to the chamber axis at the first chamber end and a second plane perpendicular to the chamber axis at a first distance d1 from the first plane selected from the range of 0-50% of the chamber length $l_c$, such as from the range of 0-40% of $l_c$, especially from the range of 0-30% $l_c$, such as from the range of 0-20% $l_c$, especially 0-15% $l_c$, such as from the range 0-10% $l_c$.

In further embodiments, the laser-based heating system may be configured to provide the laser radiation substantially centered with respect to the chamber height and chamber width, e.g., at a location with the first distance d1 from the first chamber end and centered with respect to a cross-section (at the location) of the hosting chamber perpendicular to the chamber length. For example, in an embodiment, the chamber height may be 100 μm and the chamber width may be 600 μm, and the laser radiation may be provided at a distance of about 50 μm from the top (and bottom) wall segment of the chamber wall of the hosting chamber, and of about 300 μm from a left (and right) side wall segment of the chamber wall of the hosting chamber. Providing the laser radiation at a central location (with respect to chamber height and chamber width) may provide the benefit that the bubble (edge) may move towards the second chamber end along a substantially symmetrical hosting chamber, which may result in more consistent jet generation and/or a higher jet velocity.

The laser-based heating system may be configured to provide laser radiation to the chamber wall and/or the liquid for a heating time period, i.e., the laser-based heating system may be configured to bring the liquid to a boil by supplying laser radiation for a heating time period. The heating time period may be selected based on various parameters, including laser properties, dynamics of the liquid, a desired ejection frequency, and a desired energy efficiency. For example, a relatively short heating time period, such as a 500 ns pulse, may require a high-energy pulse and thereby be energy-inefficient; and a relatively long heating time period, such as 2 minutes, may cause unpredictable bubble formation due to heat dissipation, i.e., a long heating time period can increment the temperature of the whole liquid volume, which may change its chemical properties. Hence, in embodiments, the heating time period may be selected to induce only a local heating in the liquid, for example wherein a local heating area, especially a local heating area wherein the liquid is heated by at least 5° C., such as at least 20° C., is smaller than about $1000*10^3$ μm$^3$, such as smaller than about $800*10^3$ μm$^3$, especially smaller than about $500*10^3$ μm, i.e., the heating time period may be selected such that the bubble generation is sufficiently fast that the heat does not substantially dissipate throughout the liquid. Hence, in embodiments, the laser-based heating system may be configured to provide laser radiation to the chamber wall and/or to the liquid for a heating time period selected from the range of 0.1 ms-10 s, such as from the range of 0.2 ms-1 s, especially from the range of 0.5 ms-100 ms, such as from the range of 1 ms-500 ms, especially from the range of 2 ms-5 ms.

In further embodiments, the laser-based heating system may be configured to provide laser radiation to the chamber wall and/or to the liquid at a local irradiation area smaller than about $1000*10^3$ μm$^3$, such as smaller than about $800*10^3$ μm$^3$, especially smaller than about $500*10^3$ μm$^3$.

The jet ejection frequency may depend on the heating time period. A shorter heating time period (for example, at a larger power) may facilitate a higher jet ejection frequency, as less time is needed per jet ejection. The laser-based heating system may provide laser radiation to the chamber wall and/or the liquid for a duration longer than the heating time period. Especially, in embodiments, the laser-based heating system may provide laser radiation to the chamber wall and/or the liquid such that the liquid is brought to a boil successively, especially wherein the hosting chamber is (at least partially) refilled (up to a second distance d2) with liquid in between successive jet ejections. In further embodiments, the hosting chamber may be passively or actively refilled with liquid, especially passively. In further embodiments, the hosting chamber may be actively refilled with liquid, especially artificially, such as with a pump.

The laser-based heating system may be configured to provide laser radiation to the chamber wall and/or the liquid with a power suitable to bring the liquid to a boil during the heating time period. Hence, in embodiments, the laser-based heating system may be configured to provide laser radiation with a power of at least 50 mW, especially at least 75 mW, such as 100 mW, especially at least 150 mW, such as at least 200 mW, especially at least 250 mW, such as at least 300 mW, especially at least 350 mW, such as at least 400 mW. In further embodiments, the laser-based heating system may be configured to provide laser radiation with a power of at most 2000 mW, such as at most 1500 mW, especially at most 1300 mW, such as at most 1100 mW, especially at most 500 mW.

The power required by the laser-based heating system may be provided by a portable battery, i.e., the power requirements of the laser-based heating system may be sufficiently low that the laser-based heating system can be powered by a (commercially available) portable battery. Hence, in embodiments, the jet injection system comprises a battery holder configured to hold a battery, wherein the battery holder is functionally coupled to the laser-based heating system such that the battery powers the laser-based heating system. In further embodiments, the jet injection system may be a handheld device.

In specific embodiments, the jet injection system comprises a battery holder configured to hold a battery, wherein the battery holder is functionally coupled to the laser-based heating system such that the battery powers the laser-based heating system, especially wherein the laser-based heating system is configured to provide laser radiation with a power of at most 500 mW.

Providing the laser radiation may lead to boiling of the liquid, resulting in the formation of a bubble (having a bubble edge) expanding/moving to the second chamber end, thereby displacing the liquid and generating a jet exiting the hosting chamber at the second chamber end. The second chamber end may be configured to adjust and/or guide the jet.

Hence, in embodiments, the second chamber end may comprise a nozzle configured to adjust and/or guide the jet. Similarly, in further embodiments, the second chamber end may comprise a tapering configured to adjust and/or guide the jet. A nozzle and/or tapering may facilitate the generation of jets with a higher velocity. However, a nozzle and/or tapering may also reduce jet stability.

In further embodiments, the jet injection system, especially the microfluidic device, may comprise a posterior chamber (essentially) defined by a posterior chamber wall, especially by an inner posterior wall surface, wherein the posterior chamber is arranged downstream from the second chamber end relative to the first chamber end. The posterior chamber may have a posterior chamber length $l_g$ parallel to the chamber axis A, a posterior chamber width $w_g$ parallel to the chamber width $w_c$, and a posterior chamber height $h_g$ parallel to the chamber height $h_c$. Especially, the posterior chamber width $w_g$ >the chamber width $w_c$ and the posterior chamber height $h_g$>the chamber height $h_c$. The posterior chamber may be configured such that the jet essentially does not touch the wall(s) of the posterior chamber. The posterior chamber may comprise a posterior chamber opening coinciding the second chamber opening, i.e., the posterior chamber may be arranged such that the second chamber opening is essentially free (not blocked).

The posterior chamber may be provided during the construction of the microfluidic device, especially wherein the hosting chamber is prefilled with the liquid. In further embodiments, the posterior chamber may be configured for breaking off part of the posterior chamber, especially downstream from the hosting chamber, prior to jet ejection. Hence, the hosting chamber may be prefilled with a liquid, and part of the posterior chamber may be broken off such that an opening to air is provided. Such embodiment may be beneficial for disposable microfluidic devices suitable for a single injection.

In further embodiments, the posterior chamber may be configured to be placed on the subject, especially such that a predetermined distance is provided between the second chamber end and the subject. In this way, the distance to the skin may always be the same.

In embodiments, the jet ejection system may be configured for the injection of a jet into a subject, i.e., for the ejection of a jet suitable for the penetration of the surface of a subject such that the jet enters the subject.

The term "subject" herein may refer to an animal or an object. For example, the subject may be a human. Such human may receive a medical or cosmetic injection, especially a cosmetic injection, with the jet injection system. Similarly, the subject may be a pet or a farm animal receiving an injection for veterinary purposes, such as a vaccination. The subject may also be a coating, wherein, for example, the jet injection can be used to functionalize the coating. For example, an object (metal, plastic, etc.) may be coated for a specific function, and locally the surface properties of the coating can be altered by bringing a liquid jet into a (specific) entry point. In particular, implants may require that some parts are hydrophobic and other parts are hydrophilic; the jet can provide the complementary property that the coating does not have. It could also be that the jet comprises a substance suitable to cure the coating (like two-component glue).

Hence, in further embodiments, the subject may comprise an animal, especially a human, or especially a pet or a farm animal. In further embodiments, the subject may comprise an object.

In embodiments, the jet injection system may be configured for positioning the jet injection system on a subject such that a jet ejected by the jet injection system is injected into the subject.

In further embodiments, the jet injection system may comprise a distance holder for arranging the jet injection system on a subject with a desired distance between the second chamber end and the subject. In further embodiments, the jet injection system, especially the microfluidic chamber, may comprise a posterior chamber comprising the distance holder, i.e., the posterior chamber may be configured for arranging the jet injection system on a subject with a desired distance between the second chamber end and the subject. Hence, the distance holder may comprise the posterior chamber or the posterior chamber may be configured as distance holder.

In embodiments, the jet injection system may be configured to provide a first jet to a subject surface location, especially a first jet suitable to break the surface of the subject at the subject surface location, and to subsequently provide a subsequent jet, especially a plurality of subsequent jets, at the subject surface location. The first jet and subsequent jet(s) may enable injecting more (different types of) liquid into the subject than a single injection (jet). The first jet may break the surface of the subject, thereby reducing the requirements for injection of subsequent jets. The subsequent jet(s) may, for example, successfully inject with a lower jet velocity (than the first jet). Similarly, the subsequent jet(s) may successfully inject a higher volume of liquid with the same jet velocity (relative to the first jet). Further, the subsequent jet(s) may inject a different liquid into the subject. Especially, the first jet may comprise liquid devoid of a functional component, such as a pharmaceutical and/or a nutraceutical, and the second jet may comprise liquid comprising the functional component, such as a pharmaceutical and/or a nutraceutical.

In further embodiments, the jet injection system may comprise a plurality of hosting chambers. In such embodiments, the jet injection system may be configured to eject multiple jets at the same time. Especially, the jet injection system may be configured to inject multiple jets at a subject surface location at the same time, i.e., the respective chamber axes of the plurality of hosting chamber may intersect the subject surface location; the axes focus on the subject surface location. Such simultaneous multi-jet injection may facilitate the injection of more liquid before the opening or orifice pierced in the subject being injected into closes, which may otherwise leave liquid not injected (splash-back). Furthermore, simultaneous multi-jet injection may also facilitate reaching deeper into the subject.

In embodiments, the jet injection system may comprise or be functionally coupled to a control system configured to control the jet injection system. Especially, the control system may further be functionally coupled to a sensor system configured to measure a parameter related to the subject. For example, the sensor system may provide a sensor signal, especially an image, related to the surface of the subject to the control system, and the control system may determine a suitable subject surface location for the jet injection based on the sensor signal, and the control system may control the jet injection system to inject a jet at the subject surface location. Especially, the jet injection system may be functionally coupled to a robotic arm controlled by the control system.

The sensor system may be configured to measure a parameter related to subject features relevant for jet injection. For example, the sensor system may be configured to measure a parameter related to one or more of subject toughness (such as skin toughness), pressure, subsurface features, and other features relevant for jet injection, and to provide a sensor signal to the control system, wherein the control system is configured to control one or more jet ejection properties based on the sensor signal. For example, the control system may be configured to increase the jet velocity if the sensor signal indicates that a subject, such as a human skin, is particularly tough, or similarly, may reduce the jet velocity if the sensor signal indicates that the subject is particularly fragile. The jet velocity may, for example, be increased (reduced) by decreasing (increasing) the amount of liquid to displace by decreasing (increasing) the second distance d2 and/or by increasing (decreasing) the first distance d1, or by increasing (reducing) the laser power.

In specific embodiments, the jet velocity may be controlled by providing a second jet perpendicular to the jet, wherein the second jet intersects the jet, i.e., the second jet interferes with the jet and may thereby reduce the jet velocity.

In further specific embodiments, the jet velocity may be controlled by providing two initial jets at an angle such that they converge and form a combined jet, wherein the combined jet has a higher jet velocity than either of the two initial jets.

In further embodiments, the sensor system may comprise an air pulsation system configured to provide an air pulse to a subject and to measure a subject response. For example, the air pulsation system may comprise a tonometry system, especially a tonometry system similar to those configured to measure eye pressure, more especially a tonometry system configured to measure eye pressure.

In further embodiments, the sensor system may comprise one or more illumination-based sensor systems configured to provide polarized and/or non-polarized illumination to the subject and to measure (internal) reflection of the illumination. For example, different wavelengths of light may penetrate to different (skin) depths and may thereby be used to determine subsurface structures in the subject. The sensor system may then provide a sensor signal to the control system, especially wherein the sensor signal is related to the measured (internal) reflection. The control system may then, for example, control the jet velocity and/or jet volume based on the sensor signal such that the jet is injected at a desired depth and in a desired volume.

In embodiments, the jet injection system may be part of or may be functionally coupled to a robotic injection system, wherein the robotic injection system comprises the control system functionally coupled to the sensor system. For example, in specific embodiments, the robotic injection system may comprise a tattoo robot configured to inject jets into the skin of a subject to provide a tattoo. In further embodiments, the robotic injection system may comprise an autonomous robotic injection system.

In yet further embodiments, the jet injection system may be part of or may be functionally coupled to a desktop printer.

In specific embodiments, the jet injection system may comprise (i) a microfluidic device for jet ejection and (ii) a laser-based heating system, wherein: the microfluidic device comprises a hosting chamber defined by a chamber wall, wherein the hosting chamber is configured to host a liquid, the hosting chamber having a chamber height $h_c$ selected from the range of 5-400 μm, a chamber width $w_c$ selected from the range of $2h_c$-$10h_c$, and a chamber length $l_c$ defined by a first chamber end and a second chamber end, wherein the second chamber end comprises a first chamber opening for jet ejection from the hosting chamber; the laser-based heating system is configured to provide laser radiation to one or more of the chamber wall and a liquid in the hosting chamber.

In a second aspect, the invention further provides the microfluidic device for jet ejection ("liquid jet ejection"). The microfluidic device may comprise a hosting chamber (essentially) defined by a chamber wall, especially wherein at least part of the chamber wall is light transmissive for laser radiation. In embodiments, the hosting chamber may be configured to host a liquid. In embodiments, the hosting chamber may have a chamber height $h_c$ selected from the range of 5-400 μm, especially selected from the range of 80-120 μm. In further embodiments, the hosting chamber may have a chamber width $w_c$ selected from the range of 1hc-12hc, such as from the range of 2hc-10hc, especially from the range of 3hc-6hc, such as from the range of $3h_c$-$4.5h_c$ or from the range of $5.5h_c$-$6h_c$. In further embodiments, the hosting chamber may have a chamber length $l_c$ defined by a first chamber end and a second chamber end. In specific embodiments, along at least 80% of the chamber length $l_c$ the chamber height $h_c$ and chamber width $w_c$ are constant, or (when slightly not constant) one or both of the chamber height $h_c$ and chamber width $w_c$ vary with less than 10% relative to (their) respective maximum values (of the chamber height $h_c$ and the chamber width $w_c$). The second chamber end may comprise a first chamber opening for jet ejection (of at least part of the liquid) from the hosting chamber. The hosting chamber may be configured for receiving laser radiation to the chamber wall and/or to the liquid in the hosting chamber (at a location) closer to the first chamber end than to the second chamber end.

In specific embodiments, the microfluidic device may comprise a hosting chamber defined by a chamber wall, wherein the hosting chamber is configured to host a liquid, wherein at least part of the chamber wall is light transmissive for laser radiation, the hosting chamber having a chamber height $h_c$ selected from the range of 80-120 μm, a chamber width $w_c$ selected from the range of $3h_c$-$4.5h_c$ or from the range of $5.5h_c$-$6h_c$, and a chamber length $l_c$ defined by a first chamber end and a second chamber end, wherein along at least 80% of the chamber length $l_c$ the chamber height $h_c$ and chamber width $w_c$ are constant, wherein one or both of the chamber height $h_c$ and chamber width $w_c$ vary with less than 10% relative to respective maximum values, wherein the second chamber end comprises a first chamber opening for jet ejection from the hosting chamber.

In embodiments, the microfluidic device may be provided from a light-transmissive and/or mechanically robust material. The material may especially be light-transmissive, especially at least 90% light-transmissive, such as at least 99% light-transmissive, for the laser radiation, such as especially for one or more wavelengths comprised by the laser radiation. In further embodiments, the material may (essentially) be transparent for the laser radiation, especially for one or more wavelengths comprised by the laser radiation. Similarly, the material may especially be mechanically robust with respect to the (violent) bubble expansion. Hence, in specific embodiments, the microfluidic device may comprise a material selected from the group comprising silicon, glass, PDMS (polydimethylsiloxane), PMMA (poly(methyl methacrylate)), and COC (cyclic olefin copolymer). Hence, in embodiments, the microfluidic device may comprise a material selected from the group comprising silicon, glass, PDMS, PMMA, and COC, especially glass. In embodiments, the microfluidic device may be configured suitable for functional coupling to a (dedicated) laser pointer. In such embodiments, the (dedicated) laser pointer may comprise the laser-based heating system.

In a third aspect, the invention further provides a method for ejecting a jet from the jet injection system according to the invention or from the microfluidic device according to the invention, the method comprising: —a liquid provision step comprising providing the liquid to the hosting chamber; and —an ejection step comprising providing laser radiation to the chamber wall and/or to the liquid such that at least part of the liquid is boiled and a jet is ejected.

In embodiments, the ejection step may comprise providing laser radiation to the chamber wall and/or to the liquid for a heating time period selected from the range of 0.1 ms-10 s, such as from the range of 0.2 ms-1 s, especially from the range of 0.5 ms-100 ms, such as from the range of 1 ms-500 ms, especially from the range of 2 ms-5 ms.

In further embodiments, the ejection step may comprise providing laser radiation with a power of at least 50 mW, especially at least 75 mW, such as 100 mW, especially at least 150 mW, such as at least 200 mW, especially at least 250 mW, such as at least 300 mW, especially at least 350 mW, such as at least 400 mW. In further embodiments, the ejection step may comprise providing laser radiation with a power of at most 2000 mW, such as at most 1500 mW, especially at most 1300 mW, such as at most 1100 mW, especially at most 500 mW.

In embodiments, the method may further comprise: a positioning step comprising positioning the microfluidic device on a subject; and wherein the ejection step comprises injecting the jet into the subject. Especially, the positioning step may occur before the ejection step (and before or after the liquid provision step).

In embodiments, the method further comprises: a second liquid provision step comprising providing a second liquid to the hosting chamber; and a second ejection step comprising providing laser radiation to the chamber wall and/or to the liquid such that the second liquid is boiled and a second jet is ejected. Especially, the second ejection step may comprise injecting the second jet into the subject.

In embodiments, the method may be a non-medical method. In embodiments, the method may especially be a cosmetic method, or especially a sensing method.

In specific embodiments, the method for ejecting a jet from the jet injection system may comprise: a liquid provision step comprising providing the liquid to the hosting chamber; and an ejection step comprising providing laser radiation to the chamber wall and/or to the liquid such that at least part of the liquid is boiled and a jet is ejected.

The embodiments described herein are not limited to a single aspect of the invention. For example, an embodiment describing the jet injection system with respect to jet ejection may, for example, further relate to the method for ejecting a jet. Similarly, an embodiment of the jet injection system describing the microfluidic device may further relate to the microfluidic device as such. Similarly, an embodiment of the method describing an operation of the jet ejection system may indicate that the jet ejection system may, in embodiments, be suitable for the operation. For example, if the method describes adjusting the laser radiation power between subsequent jets, it may be clear that the jet ejection system, especially the laser-based heating system, may be configured to control the laser radiation power (during operation).

The terms "upstream" and "downstream" relate to an arrangement of items or features from a reference position relative to an axis (here especially the chamber axis A), wherein relative to a reference position along the axis, a first position closer to the reference position than a second position (along the axis) is "upstream" of the second position, and a third position further away from the reference position than the second position is "downstream" of the second position.

The jet injection system may be part of or may be applied in e.g. (handheld) medical devices, (handheld) cosmetic devices, assembly lines, (3D) printers, robots, sensing applications where the jet is splashed against a surface, say the skin, to obtain reproducible splashing against a sensor surface, modification of coatings or films in industrial settings.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figures 1A, 1B, 1C:
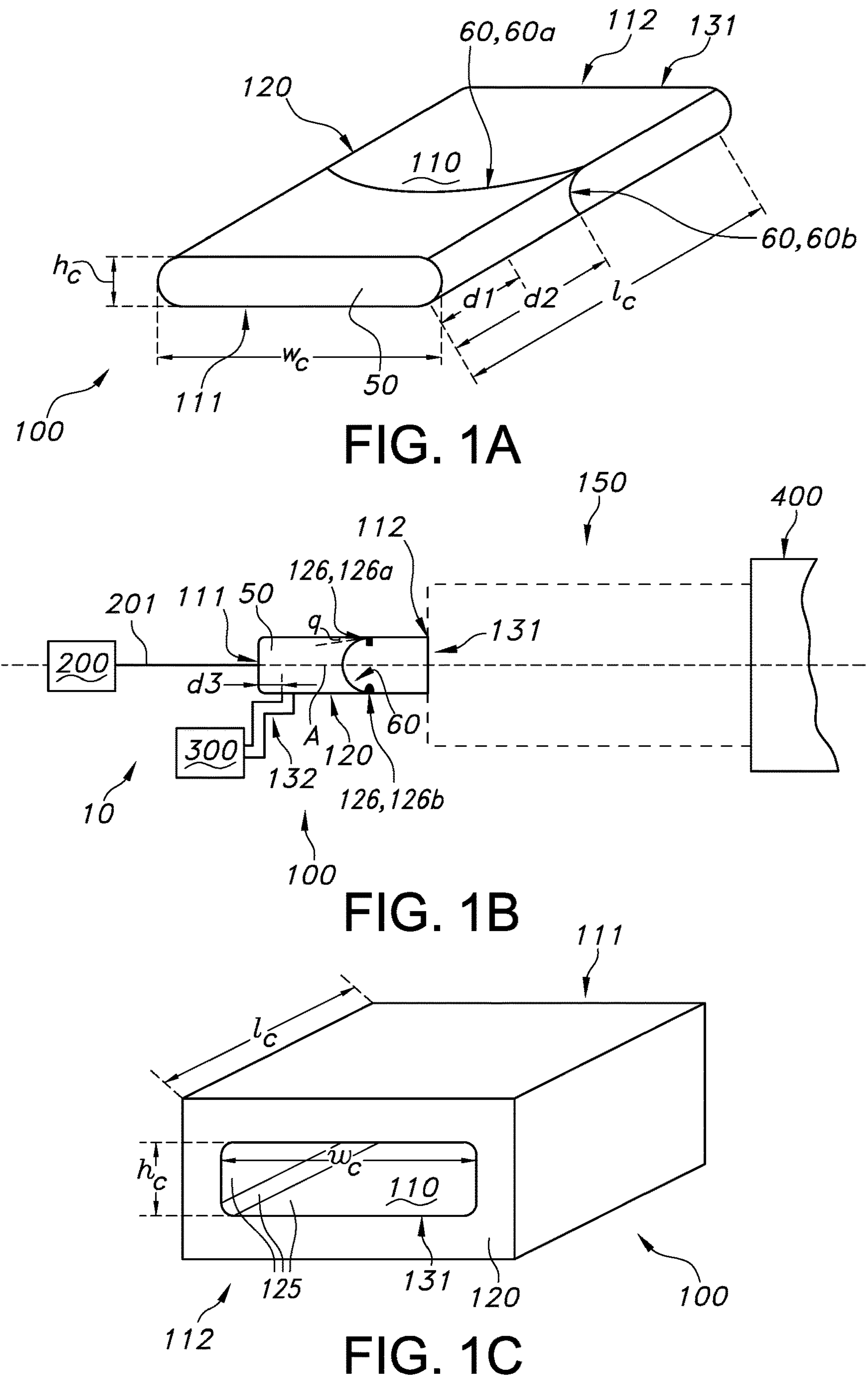
FIG. 1A-C schematically depict embodiments of the microfluidic device and the jet injection system.

FIG. 1A schematically depicts a microfluidic device 100 for jet ejection. The microfluidic device 100 comprises a hosting chamber 110 defined by a chamber wall 120. Especially, at least part of the chamber wall 120 may be light transmissive for laser radiation 201. The hosting chamber 110 is configured to host a liquid 50. The hosting chamber 110 has a chamber height $h_c$ selected from the range of 80-120 μm, a chamber width $w_c$ selected from the range of $3h_c$-$4.5h_c$ or from the range of $5.5h_c$-$6h_c$, and a chamber length $l_c$ defined by a first chamber end 111 and a second chamber end 112.

The hosting chamber may be filled with the liquid from the first chamber end 111 to a second distance d2 from the first chamber end 111. The second distance d2≤the chamber length $l_c$, here depicted as approximately 0.5 $l_c$. At the second distance d2, the liquid 50 interfaces with air and forms the meniscus 60. Specifically, FIG. 1A depicts a double meniscus 60 having a first meniscus 60, 60a and a second meniscus 60, 60b. The hosting chamber 110 may be a quasi-two-dimensional chamber which is partially filled with the liquid 50 to be ejected. The specific geometry of the hosting chamber 110 may allow the formation of a double meniscus 60 (two menisci 60) which may play a role in the self-focusing of the jet 80.

In the depicted embodiment, the laser-based heating system 200 may be configured to provide the laser radiation 201 to the chamber wall 120 and/or to the liquid 50 within a first distance d1 from the first chamber end 111, wherein d1≤0.5 chamber length $l_c$, such as ≤0.4 $l_c$. Especially, d1<d2.The second chamber end 112 comprises a chamber opening 131 for jet ejection from the hosting chamber 110. The hosting chamber 110 is configured for receiving laser radiation 201 to the hosting chamber wall 120 and/or to the liquid 50 in the hosting chamber 110, especially at a location closer to the first chamber end 111 than to the second chamber end 112.

In the depicted embodiment, the chamber height $h_c$ and the chamber width $w_c$ are constant along the entire chamber length $l_c$. In particular, the hosting chamber has a chamber axis A parallel to the chamber length $l_c$, and the cross-sectional view of the hosting chamber perpendicular to the chamber axis A is constant along the chamber axis A. In the depicted embodiment, the hosting chamber 110 has a cross-sectional shape approximating a stadium along the entire chamber length $l_c$.

In further embodiments, along at least 80% of the chamber length $l_c$ the hosting chamber 110 may have a cross-sectional shape approximating a shape selected from the group comprising a rounded rectangle, a stadium, and an oval. In the depicted embodiment, the hosting chamber 100 has a cross-sectional shape (along the chamber length $l_c$) approximating a stadium.

FIG. 1B schematically depicts the jet injection system 10 comprising (i) a microfluidic device 100 for jet ejection and (ii) a laser-based heating system 200, wherein: —the microfluidic device 100 comprises a hosting chamber 110 defined by a chamber wall 120, the hosting chamber 110 having a chamber height $h_c$ selected from the range of 5-400 μm, a chamber width $w_c$ selected from the range of $2h_c$-$10h_c$, and a chamber length $l_c$ defined by a first chamber end 111 and a second chamber end 112, wherein the second chamber end 112 comprises a first chamber opening 131 for jet ejection from the hosting chamber 110, and wherein the hosting chamber 110 is configured to host a liquid 50; —the laser-based heating system 200 is configured to provide laser radiation 201 to one or more of the chamber wall 120 and a liquid 50 in the hosting chamber 110, wherein the laser-based heating system 200 is configured to provide the laser radiation 201 to the chamber wall 120 and/or to the liquid 50 in the hosting chamber 110 closer to the first chamber end 111 than to the second chamber end 112.

In the depicted embodiment, the hosting chamber 110 comprises a contact line barrier 126 (arranged at a second distance d2) from the first chamber end 111, wherein the contact line barrier 126 is selected from the group comprising a indentation and a protrusion. In particular, the contact line barrier 126 is depicted as a protrusion, and for visualization purposes the contact line barrier comprises a square protrusion 126*a* and a rounded protrusion 126*b*. Also, for visualization purposes only, the protrusions are depicted enlarged relative to the hosting chamber 110. In further embodiments, the contact line barrier 126 may comprise one or more indentations depressed (or "recessed") into the chamber wall 120 (in contrast to the depicted protrusions protruding from the chamber wall 120).

In further embodiments, the barrier height (also "barrier depth") of the contact line barrier 126 relative to the chamber wall 120 may be selected from the range of 3-70 μ, such as from the range of 5-50 μm, especially from the range of 10-40 μm. The term "barrier height" may also be used herein to refer to the depth of a indentation into the chamber wall 120. In further embodiments, an aspect ratio of the barrier height of the contact line barrier relative to the barrier length of the contact line barrier may be at least 0.8, such as at least 1, especially at least 1.2, wherein the barrier length of the contact line barrier may be (substantially) parallel to the chamber length.

In further embodiments, the contact line barrier may run continuously over the 10 chamber wall 120, i.e., the contact line barrier may comprise a single indentation or protrusion, especially arranged at the second distance d2. In further embodiments, the contact line barrier 126 may comprise a plurality of indentations and/or protrusions. The contact line 126 barrier may be configured to facilitate providing the liquid 50 to the hosting chamber 110 up to the second distance d2, i.e., the contact line barrier 126 may facilitate providing the meniscus 60 at the second distance d2 (from the first chamber end 111). The meniscus 60 may be arranged at an initial contact angle q to the chamber wall 120 (as seen from the first chamber end 111).

In further embodiments, the contact line barrier may be arranged on part of the chamber wall, especially on a side wall segment, more especially on both side wall segments.

FIG. 1B further depicts the optional posterior chamber 150 (with hyphened lines) configured downstream from the second chamber end 112 (as seen from the first chamber end 111). The posterior chamber 150 may have a posterior chamber width $w_g$> the chamber width $w_c$ and a posterior chamber height $h_g$ >the chamber height $h_c$. In embodiments, the posterior chamber 150 may be configured to be arranged on the subject 400 to provide a desired distance between the second chamber end 112 and the subject 400, i.e., the posterior chamber may be configured as distance holder or the distance holder may comprise the posterior chamber. Especially, in the depicted embodiment, the laser-based heating system 200 is arranged downstream from the first chamber end 111 with respect to the second chamber end 112 along the chamber axis A (parallel to the chamber length $l_c$).

The laser-based heating system 200 may be configured to provide the laser radiation 201 to the hosting chamber 110, especially to the liquid 50, via the first chamber end 111.

In the depicted embodiment, the hosting chamber 110 comprises a second chamber opening 132 arranged closer to the first chamber end 111 than to the second chamber end 112, wherein the second opening 132 is configured for providing the liquid 50 to the hosting chamber 110, especially arranged from the first chamber end 111 at a third distance d3, wherein d3<d2. The second chamber opening 132 may be configured for providing the liquid 50 to the hosting chamber 110. Especially, the jet injection system 10 further comprises a fluid supply 300 configured for providing the liquid 50 to the hosting chamber 110, wherein the fluid supply 300 is functionally coupled to the second chamber opening 132. In further embodiments, the hosting chamber 110 may comprise a plurality of second chamber openings 132, especially wherein at least two of the plurality of second chamber openings 132 are configured to supply different fluids, especially different liquids, to the hosting chamber 110.

FIG. 1C schematically depicts the microfluidic device 100 from the side to which will be ejected, i.e., from the side of the second chamber end 112. The second chamber end 112 comprises a first chamber opening 131 for jet ejection from the hosting chamber 110. The hosting chamber 110 is defined by the chamber wall 120, especially by the inner chamber surface 125, as can be clearly seen from this perspective. In the depicted embodiment, the hosting chamber 110 has a shape approximating a rounded rectangle.

Figure 2:
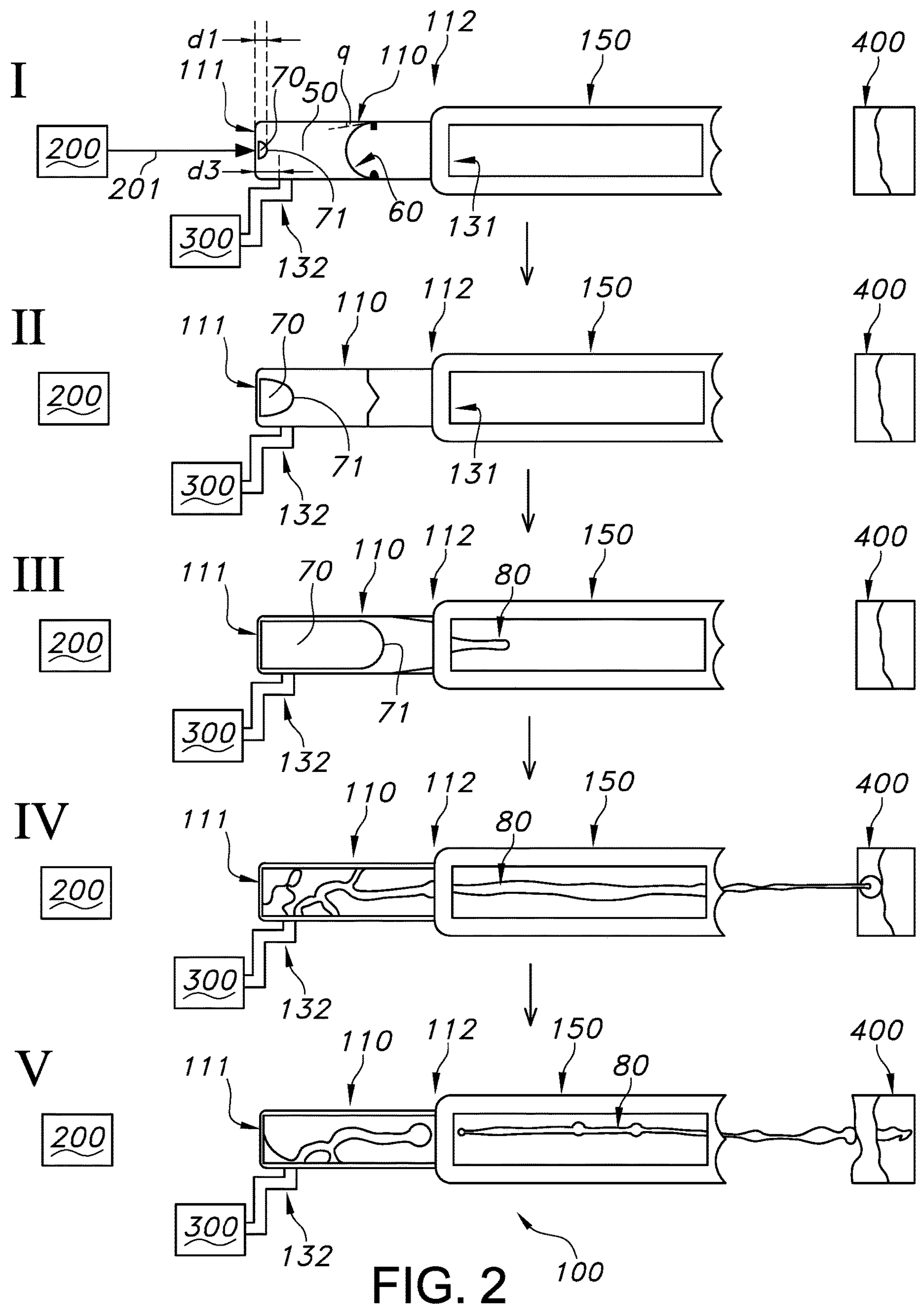
FIG. 2 schematically depicts an example of an ejection of a jet with the jet ejection system.

FIG. 2 schematically depicts experimental observations of an ejection of a jet 80 with an embodiment of the jet injection system 10. The laser-based heating system 200 provides laser radiation 201 to the liquid 50 via the first chamber end 111. Specifically, in the depicted embodiment, the laser-based heating system 200 comprises a continuous wave laser source, and the liquid 50 comprises a dye suitable for absorbing energy (heat) from the laser radiation 201. Hence, in the corresponding embodiment, at least part of the chamber wall 120 is light transmissive for laser radiation 201. In further embodiments, however, at least part of the chamber wall 120 may comprise a material configured to absorb the laser radiation 201 for heating the liquid indirectly.

At timepoint t=0 a bubble 70 forms near the first chamber end 111; timepoint I (t=10 μs) depicts the bubble 70 just after having been formed. For visualization purposes, the laser-based heating system 200 is depicted as still providing laser radiation 201, however, the laser-based heating system 200 does not need to provide laser radiation 201 after bubble 70 generation. The bubble 70, especially the bubble edge 71, rapidly expands and moves towards the second chamber end as can be seen at time points II (t=22 μs) and III (t=73 μs). At timepoint III the generation of a jet 80 is clearly visible. At about time point IV (t=276 μs) the jet penetrates the subject 400. In the depicted example the subject 400 comprises an agar gel with a 1% agar, approximately corresponding to the toughness of the dermis layer of human skin. Time point V (t=467 μs) clearly depicts a successful injection into the subject 400, with part of the jet 80 still moving towards the subject 400.

Figures 3A, 3B, 3C:
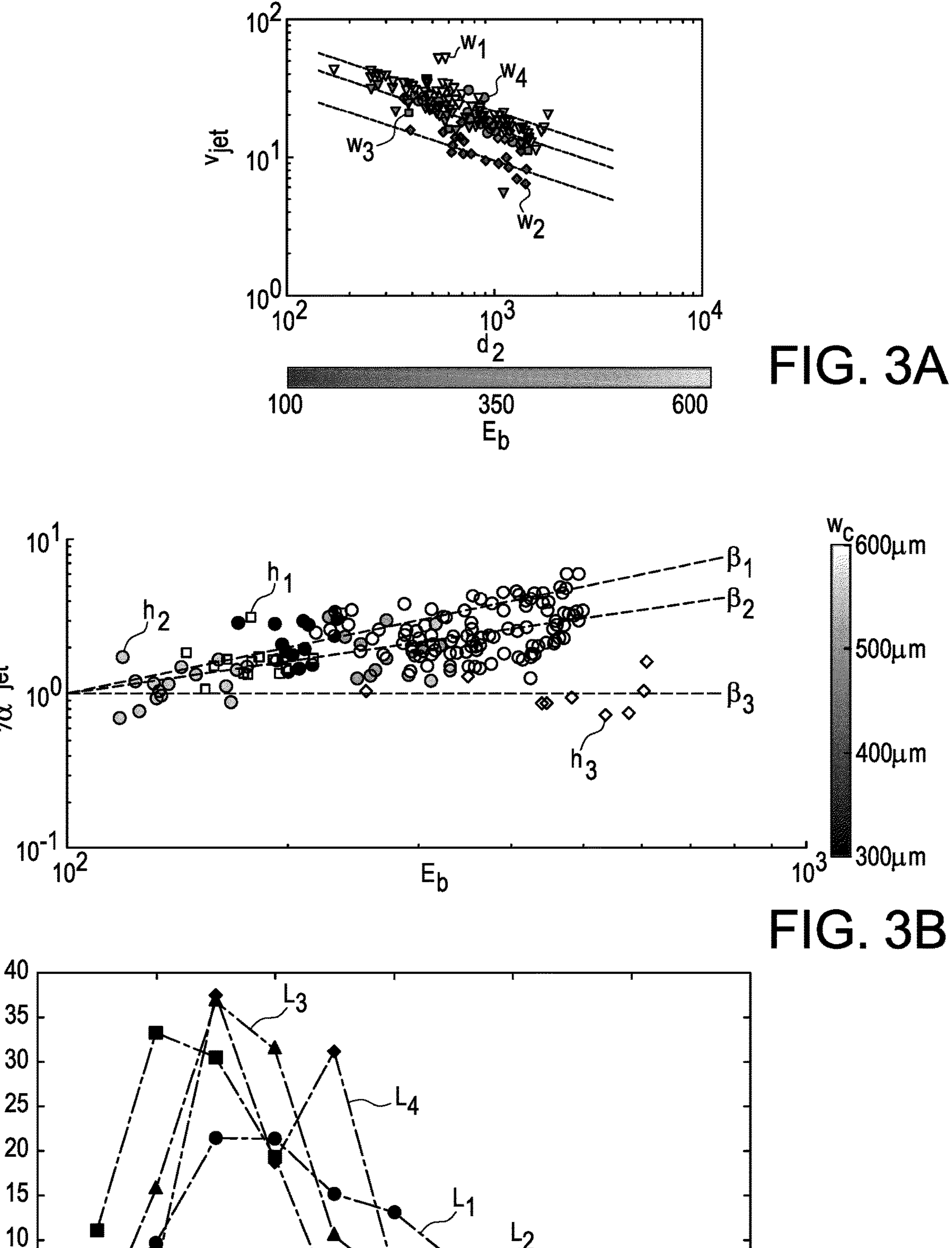
FIG. 3A-C depict experimental observations obtained using the jet injection system and the method according to the invention. The schematic drawings are not necessarily on scale.

FIGS. 3A-C depict experimental observations obtained using the jet injection system 10 and the method according to the invention. Specifically, FIGS. 3A-C depict experimental observations with varying microfluidic device dimensions and/or different second distances d2. The second distance d2 defines the position of the meniscus 60. The experiments were performed with a continuous wave laser diode, with a laser power of about 500 mW, and with a heating time period of 10 ms. The bubble energy $E_b$ (in μJ) was determined using the formula:

$$E_b = \frac{1}{2}\rho V v^2$$

wherein ρ is the liquid density, V the total liquid volume in the hosting chamber 110, and v 10 the bubble growing speed. The jet velocities were determined based on video recording.

FIG. 3A depicts observations of the jet velocity $v_{jet}$ in m/s as a function of the second distance d2 in μm for hosting chambers 110 of different dimensions. Specifically, the hosting chambers 110 used here all have a height $h_c$ of 100 μm and a length $l_c$ of 1800 μm, however, the hosting chambers 110 have varying widths $w_c$: $w_1$ (triangles)–600 μm; $w_2$ (diamonds)–500 μm; —$w_3$ (squares)–400 μm; and $w_4$ (circles)–300 μm. The hashing of the symbols indicates the bubble energy $E_b$ in μJ from 100-600 μJ (see legend).

As can be seen from the figure, for each of the hosting chamber widths $w_c$, the jet velocity is inversely correlated with the second distance d2, which may be due to the increased volume of liquid in the hosting chamber. The jet velocity appears to approximately follow a power law in relation to the second distance:

$$v_{jet} \propto d2^{-k}$$

wherein k is an attenuation factor, which appears to be about 0.5. Furthermore, there appears to be an anti-resonant configuration for $w_2(w_c=500\ \mu m)$ as the energy transfer (and resulting jet velocity) appears to be lower. Hence, for the specific chamber height $h_c$ (and optionally also chamber length $l_c$), it may be preferable to have a chamber width $w_c \leq 490$ μm or ≥510 μ, such as ≤450 μm or ≥550 μm, i.e., the chamber width $w_c$ may be selected from the range of $2h_c$-$4.9h_c$, especially from the range of $3h_c$-$4.5h_c$, or the chamber width $w_c$ may be selected from the range of $5.1h_c$-$10h_c$, especially from the range of $5.5h_c$-$6h_c$.

For the observations depicted in FIG. 3B and FIG. 3C, the second distance was varied between 200 μm and 1800 μm.

FIG. 3B depicts observations of 1/α * jet velocity $v_{jet}$ in m/s as a function of the bubble energy $E_b$ in μJ for hosting chambers 110 of different dimensions, wherein a corresponds to a coefficient of proportionality related to the amount of liquid to be displaced. The coefficient of proportionality a increases with increasing chamber height $h_c$: for $h_c$=50 μm, α=6; for $h_c$=100 μm, α=9; and for $h_c$=150 μm, α=12.

Specifically, the hosting chambers 110 used for FIG. 3B all have a chamber length $l_c$ of 1800 μm. The hosting chambers 110 have varying chamber heights $h_c$: $h_1$ (squares)–50 μm; $h_2$ (circles)–100 μm; and $h_3$ (diamonds)–150 μm. Further, the hashing of the symbols indicates chamber width $w_c$ in the range of 300-600 μm (see legend).

As can be seen from the figure, the relation between bubble energy $E_b$ and jet velocity $v_{jei}$ varies for hosting chambers with different chamber heights $h_c$. It appears that the jet velocities are correlated with the bubble energy $E_b$ in dependence of the chamber height $h_c$ following the equation:

$$v_{jec} \cong \alpha E_b^{\beta}$$

wherein α is the coefficient of proportionality, $E_b$ is the bubble energy, and β is an exponent decreasing with chamber height $h_c$. for each chamber height, the corresponding value for β is depicted in FIG. 3B: hi (50 ,lm) corresponds to (31=1; $h_2$ (100 ,lm) corresponds to (32=0.7; and $h_3$ corresponds to $\beta_3=0$. Hence, for a hosting chamber with a chamber height $h_c$ of 150 μm, it appears that the jet ejection velocity is (largely) independent of the bubble energy $E_b$, especially with laser power between 350 mW and 1100 mW.

Hence, a jet injection system 10 comprising a hosting chamber 110 according to the invention with a chamber height $h_c$ of 150 μm may essentially provide consistent jet ejection velocities, even if the jet injection system 10 comprises a relatively inconsistent laser-based heating system in terms of laser power. Hence, in specific embodiments, the hosting chamber 110 may have a chamber height $h_c$ of (approximately) 150 μm. Such embodiment may be beneficial as consistent jet ejection velocities may be provided with a relatively poor (and/or cheap) laser-based heating system.

The highest observed jet velocities in FIG. 3B correspond to hosting chambers with a chamber height $h_c$ of about 100 μm. Hence, in embodiments, the hosting chamber may have a chamber height $h_c$ selected from the range of 80-120 μ, such as (approximately) 100 μm.

FIG. 3C depicts the frequency fin percentages of observing jet velocities $v_{jet}$ in m/s for hosting chambers with varying chambers widths $w_c$. The hosting chambers all have a chamber height $h_c$ of 100 μm and a chamber length $l_c$ of 1800 μm. The lines correspond to hosting chambers with different chamber widths $w_c$: $L_1$-600 μm; $L_2$-500 μm; $L_3$-400 μm; $L_4$-300 μm.

Jet velocities suitable for jet injection are observed for all chamber widths $w_c$. In general, however, the hosting chambers with chamber widths $w_c$ of 300 μm, 400 μm or 600 μm do appear to provide higher jet velocities than hosting chambers width a chamber width $w_{c=}$ of 500 μm. The highest jet velocities correspond to hosting chambers with a chamber width $w_c$ of about 600 μm, for which velocities close to 60 m/s are observed. Hence, in embodiments, the hosting chamber may have a chamber width $w_c \geq 5.5\ h_c$, especially a chamber width $w_c$ selected from the range of 5.5-6.5 $h_c$, such as (approximately) 6 $h_c$.

The term "plurality" refers to two or more. Furthermore, the terms "a plurality of" and "a number of" may be used interchangeably.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%. Moreover, the terms "about" and "approximately" may also relate to 90% or higher, such as 95% or higher, especially 99% or higher, even more especially 99.5% or higher, including 100%. For numerical values it is to be understood that the terms "substantially", "essentially", "about", and "approximately" may also relate to the range of 90%-110%, such as 95%-105%, especially 99%-101% of the values(s) it refers to.

The term "comprise" includes also embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The term "further embodiments" may refer to embodiments comprising the features of the previously discussed embodiments, but may also refer to an alternative embodiments.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", "include", "including", "contain", "containing" and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings. Moreover, if a method or an embodiment of the method is described being executed in a device, apparatus, or system, it will be understood that the device, apparatus, or system is suitable for or configured for (executing) the method or the embodiment of the method respectively.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A jet injection system (10) comprising (i) a microfluidic device (100) for jet ejection and (ii) a laser-based heating system (200), wherein:

the microfluidic device (100) comprises a hosting chamber (110) defined by a chamber wall (120), wherein the hosting chamber (110) is configured to host a liquid (50), the hosting chamber (110) having a chamber height he selected from a range of 5-400 μm, a chamber width $w_c$ selected from a range of $2h_c$-$10h_c$, and a chamber length $l_c$ defined by a first chamber end (111) and a second chamber end (112), wherein the second chamber end (112), wherein along at least 80% of the chamber legnth $l_c$ the hosting chamber (110) has a cross-sectional shape selected from the group consisting of a rounded rectangle, a stadium, and an oval, wherein the second chamber end (112) comprises a first chamber opening (131) for jet ejection from the hosting chamber (110); and the laser-based heating system (200) is configured to provide laser radiation (201) to one or more of the chamber wall (120) and a liquid (50) in the hosting chamber (110).

2. The jet injection system (10) according to claim 1, wherein at least part of the chamber wall (120) is either light transmissive for the laser radiation (201) or comprises a material configured to absorb the laser radiation (201).

3. The jet injection system (10) according to claim 1, wherein the laser-based heating system (200) is configured to provide the laser radiation (201) to one or more of the chamber wall (120) and the liquid (50) within a first distance d1 from the first chamber end (111), wherein d1≤0.4*$l_c$.

4. The jet injection system (10) according to claim 1, wherein the laser-based heating system (200) is configured to provide the laser radiation (201) to the hosting chamber (110) via the first chamber end (111).

5. The jet injection system (10) according to claim 1, wherein the chamber wall (120) comprises an inner chamber surface (125), wherein at least part of the inner chamber surface (125) is hydrophobic.

6. The jet injection system (10) according to claim 1, wherein along at least 80% of the chamber length $l_c$ the chamber height $h_c$ and chamber width $w_c$ are constant, or wherein one or both of the chamber height $h_c$ and chamber width $w_c$ vary with less than 10% relative to respective maximum values.

7. The jet injection system (10) according to claim 1, wherein the chamber height he is selected from a range of 80-120 μm, and wherein the chamber width $w_c$ is selected from a range of $3h_c$-$6h_c$.

8. The jet injection system (10) according to claim 1, wherein the hosting chamber (110) comprises a contact line barrier (126) arranged at a second distance d2 from the first chamber end (111), wherein the contact line barrier (126) is selected from the group consisting of an indentation and a protrusion.

9. The jet injection system (10) according to claim 1, wherein the laser-based heating system (200) comprises a continuous wave laser source, and wherein the laser-based heating system (200) is configured to provide laser radiation with a power of at least 50 mW and at most 2000 mW.

10. The jet injection system (10) according to claim 1, wherein the hosting chamber (110) comprises a second chamber opening (132) arranged closer to the first chamber end (111) than to the second chamber end (112), wherein the second chamber opening (132) is configured for providing the liquid (50) to the hosting chamber (110), wherein the jet injection system (10) further comprises a fluid supply (300) configured for providing the liquid (50) to the hosting chamber (110), wherein the fluid supply (300) is functionally coupled to the second chamber opening (132).

11. The jet injection system (10) according to claim 1, wherein the jet injection system (10) is a handheld device, and wherein the jet injection system (10) comprises a distance holder for arranging the jet injection system (10) on a subject (400) with a desired predetermined distance between the second chamber end 112 and the subject (400).

12. A microfluidic device (100) comprising a hosting chamber (110) defined by a chamber wall (120), wherein the hosting chamber (110) is configured to host a liquid (50), wherein at least part of the chamber wall (120) is light transmissive for laser radiation (201), the hosting chamber (110) having a chamber height $_c$ selected from a range of 80-120 μm, a chamber width $w_c$ selected from a range of $3h_c$-$4.5h_c$ or from a range of $5.5h_c$-$6h_c$, and a chamber length $l_c$ defined by a first chamber end (111) and a second chamber end (112), wherein along at least 80% of the chamber length $l_c$ the chamber height $h_c$ and chamber width $w_c$ are constant, wherein one or both of the chamber height $h_c$ and chamber width $w_c$ vary with less than 10% relative to respective maximum values, and wherein along at least 80% of the chamber legnth $l_c$ the hosting chamber (110) has a cross-sectional shape selected from the group consisting of a rounded rectangle, a stadium, and an oval, wherein the second chamber end (112) comprises a first chamber opening (131) for jet ejection from the hosting chamber (110).

13. A method for ejecting a jet (20) from the jet injection system (10) according to claim 1 or from the microfluidic device (100) according to claim 12, the method comprising:

a liquid provision step comprising providing the liquid (50) to the hosting chamber (110); and an ejection step comprising providing laser radiation (201) to one or more of the chamber wall (120) and the liquid (50) such that at least part of the liquid (50) is boiled and a jet (20) is ejected.

14. The method according to claim 13, wherein the method further comprises:

a positioning step comprising positioning the microfluidic device (10) on a subject;

and wherein the ejection step comprises injecting the jet (20) into the subject.

15. The method according to claim 13, wherein the method further comprises:

a second liquid provision step comprising providing a second liquid to the hosting chamber (110); and a second ejection step comprising providing laser radiation (201) to one or more of the chamber wall (120) and the liquid (50) such that the second liquid is boiled and a second jet is ejected.

16. The jet injection system (10) according to claim 1, wherein the jet injection system (10) is configured to provide the liquid to the hosting chamber up to a second distance d2 from the first chamber end, wherein the second distance $d2 \leq 1_c$, wherein at the second distance d2, the liquid forms a meniscus at an interface with air, wherein the meniscus comprises a double meniscus.

17. The method according to claim 14, wherein the subject comprises a human or an animal.

* * * * *